United States Patent [19]

Kan et al.

[11] Patent Number: 5,270,216
[45] Date of Patent: Dec. 14, 1993

[54] MEASUREMENT OF LOW PHOSPHONATE CONCENTRATIONS

[75] Inventors: Amy T. Kan, Houston, Tex.; Kuruvila Varughese, Damman, Saudi Arabia; John E. Oddo, Houston; Mason B. Tomson, West University Place, both of Tex.

[73] Assignee: Gas Research Institute, Chicago, Ill.

[21] Appl. No.: 835,742

[22] Filed: Feb. 13, 1992

[51] Int. Cl.$^5$ .............................. G01N 21/77
[52] U.S. Cl. ................... 436/103; 436/104; 436/105; 436/171
[58] Field of Search ............... 436/103–105, 436/164, 171

[56] References Cited

PUBLICATIONS

Rogers, L.A., K. Varughese, S. M. Prestwich, G. G. Waggett, M. H. Salami, J. E. Oddo, E. H. J. Street and M. B. Tomson, "Use of Inhibitors for Scale Control in Brine Producing Gas and Oil Wells", SPE Prod. Eng. J., pp. 77–82, Feb. 1990.

*Primary Examiner*—James C. Housel
*Assistant Examiner*—David Redding
*Attorney, Agent, or Firm*—Speckman, Pauley & Fejer

[57] ABSTRACT

A process for measurement of low levels of phosphonates in brine waters wherein the phosphonate samples are acidified with hydrochloric acid promptly upon removal from an oil or gas well to prevent phosphonate precipitation or adsorption. The hydrochloric acid acidified phosphonate is digested in the presence of an oxidizing agent at elevated temperature and pressure for sufficient time to oxidize substantially all of the phosphonate to orthophosphate. The phosphorous containing compound is extracted with an organic extractant, preferably selected from the group consisting of methyl iso-butyl ketone/cyclohexane mixture and ethyl acetate, followed by color development for absorption spectrophotometry.

20 Claims, 2 Drawing Sheets

MEASUREMENT OF LOW PHOSPHONATE CONCENTRATIONS

BACKGROUND OF THE INVENTION

1. Field of the Invention

This invention relates to measurement of low levels of phosphonate materials, particularly in brine. The process of this invention stabilizes the phosphonate sample, oxidizes the hydrochloric acid acidified phosphonate to orthophosphate in the presence of an oxidizing agent with mild heat and pressure and uses organic solvent extraction, preferably with methyl iso-butyl ketone/cyclohexane or ethyl acetate, to separate the phosphorous containing compound. The process of this invention is suitable for measurement of phosphonate concentrations of about 0.1 to about 10 milligrams per liter in gas and oil well brines with reproducibility of plus or minus about 5 percent.

2. Description of Related Art

Phosphonates are well known for their use as scale and corrosion inhibitors in gas and oil wells. Such wells usually coproduce large volumes of brine. Low concentrations of phosphonates, in the order as low as 0.16 mg/l phosphonate, can effectively prevent scale formation in operating wells. Matty, J. M., K. Vaughese, G. G. Waggett, M. B. Tomson and L. A. Rogers, Control of Scale Associated with Geopressured-Geothermal Brine Production, 6th Gulf Coast Geopressured-Geothermal Energy Conference on Mitigation of Scale Formation in Geothermal/Geopressured Energy Production, pgs. 137-147, (1985); Rogers, L. A., K. Varughese, S. M. Prestwich, G. G. Waggett, M. H. Salimi, J. E. Oddo, E. H. J. Street and M. B. Tomson, Use of Inhibitors for Scale Control in Brine Producing Gas and Oil Wells, SPE Prod. Eng. J., pgs. 77–92, (February 1990) The decision to re-treat a well is frequently not based upon well performance criteria, but upon measurement of inhibitor concentrations. Therefore, the ability to measure concentrations of phosphonates down to a range of about 0.1 to about 1.0 mg/l in brine becomes important to the decision to re-treat a well. The operational cost and loss in production during shut-ins necessary for such re-treatment is significant and is desired to be kept to minimum in good well management, even though the cost of treatment chemicals may be small.

The drop in phosphonate concentration following treatment of a well is not linear and is not entirely predictable with time following treatment. In fact, phosphonate concentration in the well fluids quickly drops from initial treatment concentration of about 10,000 mg/l and greater to about 1 mg/l or below and then levels off to a relatively steady state value of about 0.1 to about 1.0 mg/l. This relatively steady state value depends upon the brine chemistry, the type of formation, and the inhibitor chemistry. Although phosphonate levels of about 0.1 to 1.0 mg/l may be too low for effective corrosion control, they are generally adequate for scale control in production tubing and thus, from an economic standpoint, are satisfactory for continued well operation in these concentration ranges. Again, this points out the desirability of accurate measurement of phosphonate concentrations at levels of about 0.1 to about 1.0 mg/l.

Prior analytical methods for measurement of the concentration of phosphonates in brine have included:

1) Use of radioactive labelled carbon or phosphorous. These methods, which require sophisticated instrumentation, are in the developmental stages and further present the problems of availability and handling of the radioisotope as well as requiring permitting.

2) Complexation with copper, thorium, iron or magnesium. Methods of complexation of phosphorous with these metals are susceptible to numerous interferences by trace metals.

3) Inductively coupled plasma arc mass spectrometry.

4) High performance ion chromotography with or without ion suppression. Both methods 3) and 4) are in the developmental stage and require sophisticated instrumentation not normally available in the field. Also, the high salinity of the natural brine frequently interferes with these methods for phosphate analysis.

5) Oxidation of phosphonate to phosphate and colorimetric measurement of increased phosphate concentration. These methods are easy to perform, but are susceptible to interferences from trace amounts of materials, such as, calcium, barium, strontium, sulfate, sulfide and silicate as well as major ion interferences due to ions such as chloride. These methods are also susceptible to interference caused by turbidity. Such interferences render this method for measuring phosphonates in brine solutions limited to those containing over about 5 mg/l phosphonate, resulting in re-treatment of the well considerably before scale would begin to develop.

The analytical method most commonly used today for measurement of phosphonate concentration is the "Hach Method" developed at Hach Chemical Company. Kindel, L. E., Determination of Low Concentrations of the Dequest Products Via Persulfate Digestion, Special Report No. 7823, Monsanto Industrial Chemicals Company, St. Louis, Mo. 63116, (January 7,1972) In the Hach Method, phosphonates are oxidized to phosphate by UV/persulfate, and the increased phosphate concentration measured as the phosphomolybdate blue complex. Standard Methods for measurement of phosphates in natural and waste waters using the phosphomolybdate blue complex is described in Cleseri, L. S., A. E. Greenberg, R. R. Trussell, Standard Methods for the Examination of Water and Wastewater, 4500-P Phosphorous, pgs 4–166–4–181, Published by American Public Health Association, American Water Works Association, and Water Pollution Control Federation, Washington, D.C., (1989) This method, which relies upon conversion of all of the phosphonate to phosphate, provides excellent results in about twenty to thirty minutes time for phosphonate concentrations down to about 0.02 mg/l in fresh water, but in brine, as pointed out above, the method is limited to reliable measurements of phosphonates greater than about 5 mg/l.

The desirability of oxidation of complex or polyphosphates to orthophosphates for quantitative analysis has been recognized and various improved procedures suggested. U.S. Pat. No. 3,574,551 teaches disadvantages of oxidation by boiling in sulfuric acid and suggests treatment with a first aqueous solution of a water soluble ferric salt, an alkali metal halide, and a lower fatty acid having 1 to 6 carbon atoms followed by treatment with a second solution of hydroxybenzoic acid, and a lower fatty acid. U.S. Pat. No. 4,544,639 teaches oxidation of organic phosphonates by an oxidizing agent stronger than nitric acid, such as perchloric acid, potassium permanganate, hydrogen peroxide, potassium dichromate, ozone, sodium bismuthate and ammonium peroxydisulfate in the presence of a silver ion catalyst. U.S. Pat. No. 4,741,400 teaches oxidation of phosphonates to orthophosphate by UV irradiation in the presence of potassium persulfate.

The recovery of phosphoric acid from phosphate rock including first decomposing the phosphate bearing ore with aqueous hydrochloric acid followed by extraction by water from a water insoluble organic extractant is taught by U.S. Pat. Nos. 3,449,074 and 4,353,877.

The recovery of phosphoric acid from aqueous solutions using methyl iso-butyl ketone is known, as exemplified by U.S. Pat. Nos. 3,342,580; 3,914,382; 4,353,877; and 4,127,640. U.S. Pat. No. 4,377,562 teaches solvent extraction of phosphoric acid from aqueous solutions containing at least 45 weight percent phosphoric acid using methyl iso-butyl ketone/cyclohexanol in 50/50 volume percent mixture in combination with sulfuric acid. U.S. Pat. No. 3,449,074 teaches recovery of phosphoric acid from phosphate rock involving a water immiscible extraction agent which may include cyclohexanol or ethyl acetate in which the phosphoric acid-extraction agent solution is contacted with an aqueous solution of hydrogen peroxide providing removal of titanium and vanadium from the phosphoric acid. U.S. Pat. No. 4,524,054 teaches leaching of phosphate ore with a mixture of water, sulfur dioxide and a carbonyl compound which may include methyl iso-butyl ketone.

The use of ammonium molybdate and a reducing agent to form the orthophosphate/molybdate complex imparting a blue color for absorbance measurements is known. U.S. Pat. No. 3,795,484 teaches reduction of the phosphate/molybdate complex with stannous chloride to heteropolyacid having color absorbance of about 700 nm on a spectophotometer. U.S. Pat. No. 3,796,543 teaches an improvement of reduction of the phosphate molybdate by hydrazine to prevent precipitation. U.S. Pat. Nos. 4,544,639 and 4,741,400 teach addition of molybdate or vanadate ion and reduction with a reducing agent such as ascorbic acid followed by measurement of absorbance at 625–800 nm to determine the quantity of orthophosphate.

SUMMARY OF THE INVENTION

It is an object of this invention to provide a process for reliable determination of phosphonates concentration in aqueous brine down to about 0.1 mg/l.

Another object of this invention is to provide a process for determination of phosphonate scale and corrosion inhibitor concentrations of down to about 0.1 mg/l in brine water as present in oil and gas well liquids.

Still another object is to provide a process for determination of phosphonates concentration in aqueous brine with a reproducibility of plus or minus 5 percent in which several samples may be analyzed within a few hours by one person.

These and other objects and advantages of the invention, which will become apparent upon reading the detailed description, are achieved by the process of this invention comprising the steps: acidifying promptly upon sampling the brine comprising phosphonates with hydrochloric acid in sufficient quantity to prevent phosphonate precipitation or adsorption; digesting the hydrochloric acid acidified brine in the presence of an oxidizing agent at elevated temperature and pressure for sufficient time to convert substantially all of the phosphonates to orthophosphate; adding sufficient molybdate salt suitable for reaction with orthophosphate to form a phosphomolybdate complex; separating the phosphomolybdate complex using an organic extractant; adding a color forming reagent for reaction with the phosphomolybdate complex forming a colored solution suitable for absorption spectrophotometry; and measuring the spectrophotometric absorption of the colored solution at or near characteristic absorption peaks, thereby obtaining the amounts of phosphonate in the brine sample by comparison with a known calibration curve.

The process of this invention represents improvement in the process for measurement of phosphonate concentration in oil or gas well aqueous liquids by oxidation of an aliquot sample of the phosphonate to orthophosphate, solvent extraction of phosphorous containing compound from the aqueous liquids in an organic extractant, and color development of the extracted phosphorous compound for spectrophotometric absorption wherein the improvement comprises acidifying the phosphonate sample with hydrochloric acid promptly upon removal from the well, the hydrochloric acid being present in sufficient quantity to prevent phosphonate precipitation or adsorption. Further improvement steps comprise digesting the hydrochloric acid acidified phosphonate in the presence of an oxidizing agent at elevated temperature and pressure for sufficient time to oxidize substantially all of the phosphonate to orthophosphate and organic solvent extraction, preferably using an extractant selected from the group consisting of methyl iso-butyl ketone/cyclohexane, isobutanol/benzene, and ethyl acetate.

DESCRIPTION OF PREFERRED EMBODIMENTS

Figure 1A:
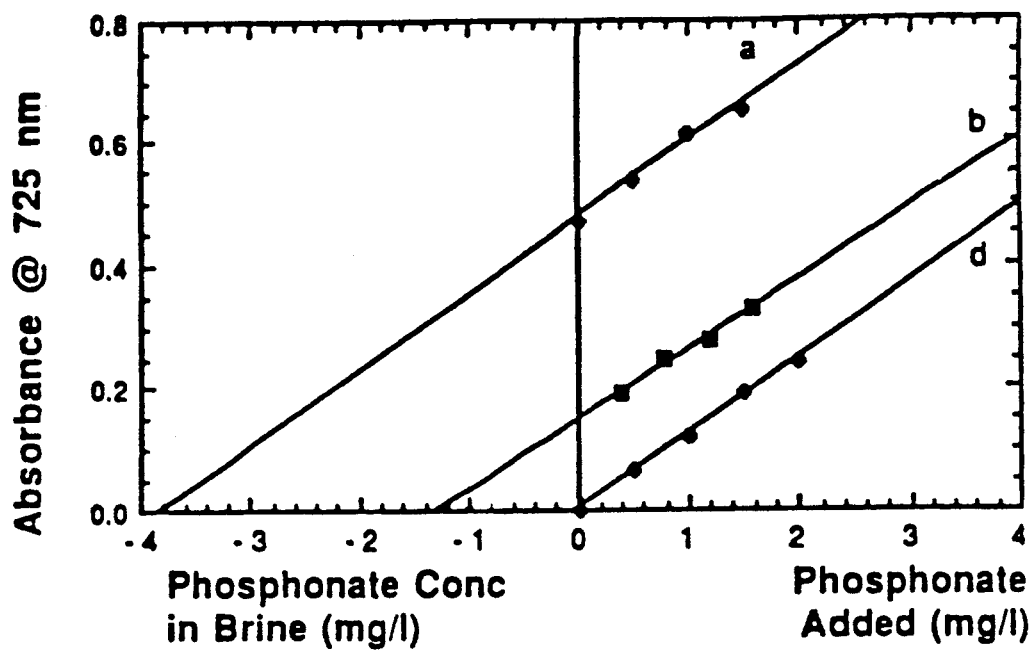
FIGS. 1A and 1B are plots of phosphonate concentration in brines measured according to the process of this invention as described in Example I.

Several components in gas producing brines have been identified as causing erroneous results in both the Hach and the Standard Methods referred to above. A number of oil and gas well brines and Houston, Texas tap water were analyzed for interferring components with respect to phosphonate analysis. The results are set forth in Table 1:

TABLE 1

| Source | *Tap | Delee | Thom | Sweet | Glad | Prud | Mish | McE |
|---|---|---|---|---|---|---|---|---|
| pH | 8.1 | — | 7.1 | 4.6 | 4.7 | 7.8 | 5.6 | 6.7 |
| Alkalinity mg/l as $HCO_3$ | 278 | 950 | 720 | 264 | 547 | 1400 | 244 | 1507 |
| Total Dissolved Solids mg/l | 452 | 41714 | 40000 | 155000 | 96340 | 21900 | 141000 | 62314 |
| Ca mg/l | 13 | 500 | 588 | 12000 | 4130 | 88 | 6952 | 2080 |

TABLE 1-continued

| Source | *Tap | Delee | Thom | Sweet | Glad | Prud | Mish | McE |
|---|---|---|---|---|---|---|---|---|
| Ba mg/l | — | 7 | — | — | — | 9 | 13 | — |
| Sr mg/l | — | — | — | — | — | — | 610 | — |
| Organic Acids mg/l as Acetic | — | 750 | — | — | — | — | — | — |
| H$_2$S mg/l | — | — | — | — | — | — | — | 455 |
| SO$_4$ mg/l | 7 | — | <5 | <5 | 17 | 375 | 340 | 1400 |

*Tap is tap water produced from Evangaline Aquifer about 1800 feet beneath Houston, Texas, U.S.A.
Delee is brine from Delee coproduction gas well, Hitchcock, Texas, U.S.A.
Thom is brine from Thompson coproduction gas well, Hitchcock, Texas, U.S.A.
Sweet is brine from Sweet Lake geopressured energy well, Louisiana, U.S.A.
Glad is brine from Gladys McCall geopressured well, Louisiana, U.S.A.
Prud is brine from crude oil production, Prudhoe Bay PBU 12-32 well, Alaska, U.S.A.
Mish is brine from crude oil production Mishriff, Saudi Arabia
McE is brine from N. McElroy Well 3550, Texas, U.S.A.

It is seen that brines contain high concentrations of dissolved solids which tend to precipitate when the brine is removed from the oil or gas well environment and reaches a new equilibrium at atmospheric temperature and pressure. Phosphonate present in the brine will coprecipitate or adsorb onto such newly formed precipitates and become unavailable for analysis. This is overcome by the process of the present invention by acidification of the brine sample at the collection site promptly upon withdrawal from the well with strong hydrochloric acid in sufficient amount to prevent phosphonate precipitation or adsorption. In the process of the present invention, hydrochloric acid is used both for stabilization of the sample prior to digestion and for digestion for conversion of phosphonate to orthophosphate.

The accuracy of both the Hach and the Standard Method procedures is dependent upon complete conversion of phosphonates to orthophosphate. We have found that when using UV/persulfate oxidation, as low as 60 mg/l acetic acid in the brine reduces conversion of phosphonate to orthophosphate to about 96% and that 600 mg/l acetic acid in the brine reduces conversion of phosphonate to orthophosphate to about 60%. As observed from Table 1 below, the Delee brine measured for organic acids exhibited 750 mg/l as acetic acid. We have found that high total dissolved solids in brine, which are primarily chloride salts, reduces the conversion of phosphonate to orthophosphate by UV/persulfate oxidation for 15 minutes as recommended by the Hach method. For example, 30,000 mg/l as NaCl total dissolved solids in brine reduces conversion of phosphonate to orthophosphate to about 93% while 150,000 mg/l as NaCl total dissolved solids in brine reduces the conversion to about 64%. Thermal digestion of the hydrochloric acid acidified brine in the presence of a persulfate oxidation agent, according to the present invention, eliminates the uncertainty of UV/persulfate oxidation conversion.

Another disadvantage of both the Hach and Standard methods referred to above, is their use of sulfuric acid as an oxidation reagent. Sulfuric acid forms insoluble salts with many metal ions, such as barium, strontium and calcium, present in most brines in widely varying amounts, as shown in Table 1. Phosphonate and phosphate tend to coprecipitate or be adsorbed onto such precipitates, again falsely reducing the phosphorous content of the sample analyzed. These disadvantages are overcome by the process of the present invention by use of hydrochloric acid which does not tend to form such precipitates.

Another problem in prior methods has been that sulfide present in sour brine reacted with the molybdate forming a complex which forms a dark blue color upon addition of a color forming reagent, thereby rendering the amount of spectrophotometric absorption due to phosphomolybdate erroneous when compared to standard phosphomolybdate calibration curves. In the process of the present invention, sulfides are stripped from acidified brines with air, thereby eliminating such interference.

It has been reported that silica, $Si^{+4}$, and copper, $Cu^{+2}$, up to 1000 mg/l and iron, $Fe^{+3}$, up to 200 mg/l do not interfere with the procedure. Boltz, D. H., Lueck, C. H., and Jakubiec, R. J., Phosphorous, Chapter 9, pgs. 337-369, Colorimetric Determination of Non-Metals, New York City, N. Y., Wiley Interscience (1978)

The solvent recommended by the Standard Method, supra, benzene/isobutanol, is not desirable since benzene is a known carcinogen and isobutanol has an obnoxious odor. Boltz and Howell, supra, recommended use of neat isobutanol, however, this requires water washing of the solvent layer to remove excess molybdenum which was extracted into the solvent phase. Use of methyl iso-butyl ketone/cyclohexane mixture or ethyl acetate in accordance with the process of the present invention eliminates the need for water wash of the organic solvent and provides a safe, more pleasant material with which to work.

In the process of the present invention, the brine sample is promptly upon collection from the well site acidified with hydrochloric acid to stabilize the phosphonates present and to prevent any other precipitation. It is preferred to use concentrated hydrochloric acid in an amount sufficient to prevent phosphonate precipitation or adsorption. We have found that about 0.5 ml to about 5.0 ml concentrated hydrochloric acid per 100 ml brine is suitable, about 1 ml to about 3 ml concentrated hydrochloric acid per 100 ml brine is preferred. It is readily apparent that larger amounts of weaker hydrochloric acid may be used to be equivalent to the above amounts. Following acidulation with hydrochloric acid according to the process of this invention, the sample may be stored until the remainder of the analytical process is convenient.

For brines having more than about 0.5 mg/l phosphonate, aliquots of about 10 to about 30 ml acidified brine are a suitable quantity for individual samply aliquot processing. In the case of brines having less than about 0.5 mg/l phosphonate, proportionately larger aliquots are suitable for individual analysis, up to about 150 ml. Aliquots of about 15 to 25 ml acidified brine are preferred for most analyses.

A suitable oxidizing agent is added to the sample aliquot for conversion of substantially all of the phosphonates to orthophosphate at elevated temperature and pressure. By the terminology substantially all, we mean greater than about 95 percent and preferably greater than about 98 percent. Suitable oxidizing agents include potassium persulfate, ammonium persulfate, concentrated perchloric acid, and nitric acid. Potassium persulfate is a preferred oxidizing agent, the strong acids being more hazardous to handle. When potassium persulfate is used, it is added to the sample aliquot in an amount of about 5 mg/ml to about 30 mg/ml, preferably about 8 mg/ml to about 12 mg/ml of acidified brine. The hydrochloric acid acidified brine is digested in the presence of an oxidizing agent at an elevated temperature and pressure for sufficient time to convert substantially all of the phosphonates to orthophosphate. Suitable digestion temperatures are about 212° to about 300° F., preferably about 240° to about 260° F., and suitable pressures are about 14 to about 30 psi, preferably about 18 to about 22 psi, for a time of about 20 to about 60 minutes, preferably about 25 to about 40 minutes, for substantially complete conversion of the phosphonate to orthophosphate.

After cooling to substantially room temperature, color development for measurement of spectrophotometric absorption is performed by adding sufficient molybdate salt suitable for reaction with all of the orthophosphate to form a phosphomolybdate complex. It is preferred to use about 5 ml to about 15 ml hydrochloric acid acidulated molybdate solution having about 39.1 gm ammonium molybdate and 210 ml concentrated hydrochloric acid diluted to about 1 liter which is added to the digested sample aliquot. An organic extractant is used to separate the phosphomolybdate complex from the aqueous phase. Suitable organic extractants include methyl iso-butyl ketone/cyclohexane mixture, isobutanol/benzene mixture, and ethyl acetate. The mixtures are suitably in proportions of about 40 to about 60 volume percent of each component. Use of the isobutanol/benzene mixture is not preferred in view of its disadvantages described above with reference to the Standard Method. A methyl iso-butyl ketone/cyclohexane mixture having about 40 to about 60 volume percent of each component is preferred. The sample aliquot with the complexing reactant and the organic extractant is shaken vigorously to form the phosphorous complex and to extract the formed phosphocomplex into the organic extractant. Usually shaking for about 10 to about 30 seconds is suitable. The aqueous and organic phases are allowed to separate and the desired sample aliquot of organic phase, about 5 ml to about 15 ml, preferably about 10 ml, is carefully withdrawn using care to not disturb the organic aqueous interface or not to withdraw any of the aqueous phase. The sample aliquot with phosphomolybdate complex is a clear, electrically neutral solution.

Alcoholic acid is used to maintain acidity of the final solution and to promote dissolution of the aqueous solution into organic solvent extractants. Alcoholic hydrochloric acid having about 30 ml to about 90 ml concentrated hydrochloric acid in about 800 ml to about 1000 ml methyl alcohol is preferred and is added to the sample aliquot with thorough mixing in about an equal amount as the sample aliquot. Ethyl alcohol can be used in place of methyl alcohol and concentrated sulfuric acid in an amount of about 20 to about 60 ml in about 800 to about 1000 ml alcohol can be used in this step since most interferring materials have been removed by the organic extraction. The alcoholic acid can be mixed with the solvent extractant sample aliquot at a volume ratio about 3:4 to about 2:1 to achieve a final solution acidity of about 0.3 to about 0.5 meq per liter. The preferred procedure is to mix about equal volumes of the alcoholic acid and solvent extractant to achieve a final acidity of about 0.34 to about 0.38 meq per liter. A color forming reagent is added with thorough mixing for reaction with the phosphomolybdate complex to form a colored solution suitable for absorption spectrophotometry. About 4 drops of stannous chloride with thorough mixing is preferred to reduce the phosphomolybdate complex forming a deep blue colored solution. We have found it important that the sample aliquot contain about 0.30N to about 0.40N hydrochloric acid, preferably about 0.34N to about 0.38N, and about 0.3 mg/l to about 0.5 mg/l stannous chloride to obtain maximum color intensity and color stability. This is about half the stannous chloride recommended by Boltz and Howell, supra. At higher acidity and stannous chloride concentrations, more intense blue color developed, but it faded in a few minutes. At lower acidity and stannous chloride concentration, a stable complex formed but had lower color intensity. We have found that using the above concentrations the absorbance is stable between about 10 and 30 minutes after color formation.

After about 10 minutes and before about 30 minutes following color formation, the absorption of the sample is measured at a wavelength of 725 nm on a spectrophotometer against a distilled water blank carried through the same procedure and the phosphate or phosphonate concentration ascertained by comparison with a calibration curve prepared from known phosphate or phosphonate samples being subjected to the same process. Spectrophotometric absorption may also be measured at 650 and 700 nm. We have found using the process of this invention on Delee brine with 3 mg/l phosphonate, the maximum absorbance is at 725 nm with the Beer-Lambert law obeyed at both 650 and 700 nm wavelength with absorbance values of 77% and 94%, respectively, of the absorbance observed at 725 nm.

We have found that the Beer-Lambert Law is obeyed for phosphonate concentrations 0.01 mg/l to about 12 mg/l. Using a standard 4 cm couvette, the lower detection limits according to the process of this invention is about 0.5 mg/l phosphonate in brines. The sensitivity ca be extended using a longer light path couvette. This has been verified using different brines and tap water with a 10 cm light path couvette. A least square curve-fitted line for the data showed an average absolute deviation of the calculated concentrations to be 5.4% and the correlation coefficient of 0.996. The sensitivity of the test process is below about 0.1 mg/l phosphonate, but most spectrophotometers are not equipped to accept a 10 cm couvette and thus this procedure is not generally suitable for field analyses.

The following examples are set forth to illustrate the process of the present invention using specific reactants and process conditions, but should not be considered as limiting the invention.

EXAMPLE I

Due to the strong adsorption of most phosphonate inhibitors on glass or metal, polyethylene or Teflon beakers, flasks and pipettes were used to contain and to transfer dilute phosphonate solutions. Concentrated hydrochloric acid was used to acidify all brines by adding 2 ml acid per 100 ml brine at the collection site to prevent precipitation in the brine. Brines containing sulfide were bubbled with air for 10 minutes prior to analysis to remove sulfur containing materials. For persulfate digestion, 20 ml of acidified brine was pipetted into a 2 oz glass vial containing 200 mg potassium persulfate ($K_2S_2O_8$) or two Hach potassium persulfate powder pillows (Hach,20847-69). The vial was closed loosely with an 18 mm Teflon faced silicone septum (Pierce Chemical Co., Rockford, Ill.) and capped. The sample was heated for 30 minutes at 212°-250° F.(15-20 psi) in a pressure cooker to oxidize the phosphonate to orthophosphate. (Lightweight sterilizer, Fisher Scientific No. 14-461-5) The sample was then cooled to room temperature for the following color development procedure.

Equal volumes of methyl iso-butyl ketone and cyclohexane were mixed forming the organic extractant and the extractant stored in a flask equipped with a Universal REPIPET dispenser, 20 ml capacity, 1% accuracy, 0.1% precision (Fisher Scientific 13-687-21). Ammonium molybdate reagent was prepared by dissolving 39.1 gms $(NH_4)_6Mo_7O_{24}\cdot 4H_2O$ in 200 ml distilled water which was added to a solution of 210 ml concentrated HCl in 400 ml distilled water, which had been cooled following preparation. The solution was diluted to 1 liter and stored in a bottle equipped with a Universal REPIPET dispenser, 10 ml capacity.

20 ml methyl iso-butyl ketone/cyclohexane extractant and 10 ml ammonium molybdate reagent was added to the sample vial and immediately shaken vigorously for 15 seconds to form the clear and electrically neutral phosphomolybdate complex (approximately $PO_3Mo_{12}O_{36}$) which was extracted into the organic extractant. After 5 minutes, allowing separation of the aqueous and solvent phases, 10 ml of the organic extractant layer was carefully withdrawn and added to a clean sample vial with an Eppendorf Maxipipetter, 10 ml capacity, 0.2-0.5% accuracy (Fisher Scientific 21-379-25), without disturbing the organic extractant/water interface or withdrawing any aqueous solution. 10 ml of alcoholic hydrochloric acid solution, prepared by adding 60 ml concentrated hydrochloric acid to 900 ml methyl alcohol and diluting to 1 liter, was added to the sample vial using a 10 ml Universal REPIPET Dispenser. With swirling, 4 drops of stannous chloride reagent prepared by mixing 0.4 gm $SnCl_2\cdot 2H_2O$ in 100 ml glycerol, was added to the sample vial and mixed thoroughly. After 10 minutes, but prior to 30 minutes, the sample absorption was measured against a blank at 725 nm on a Varian DMS-100 spectrophotometer using 4 cm couvettes. The blank was prepared by carrying 20 ml distilled water through the identical procedure as used for the sample. The phosphonate concentration was ascertained from a calibration curve formulated by treating known phosphonate standards, a stock solution of 25 mg/l diethylenetriaminepenta(methylenephosphonate) (DTPMP) 50% w/w from Monsanto, Dequest 2060, through the identical procedure used for the sample.

Figure 1B:
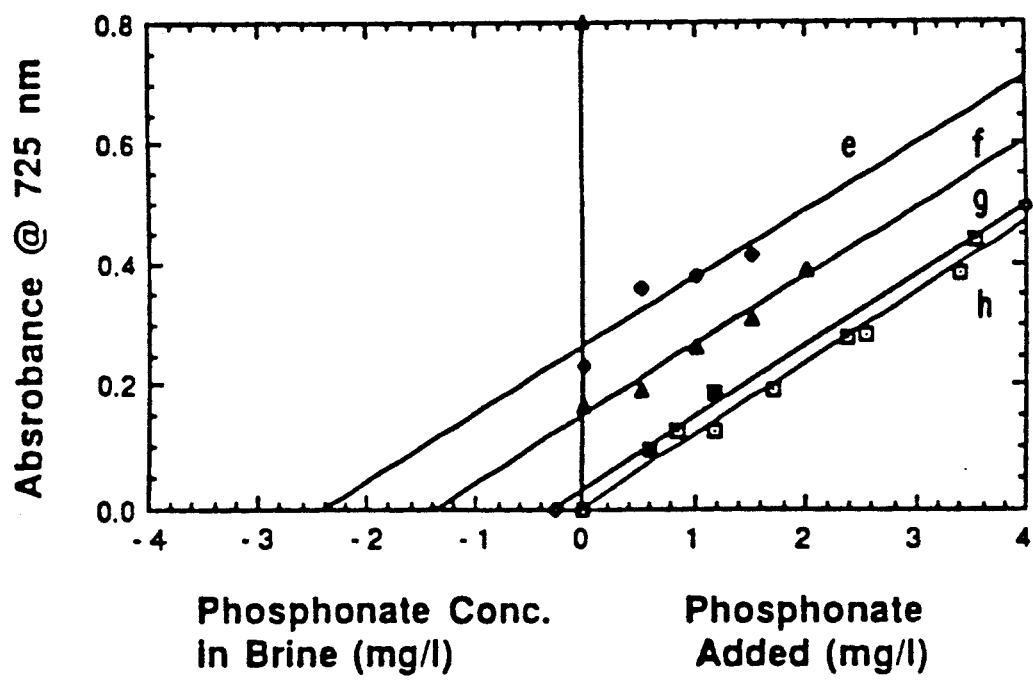

The standard additions method was used to determine the concentration of phosphate in a number of well brines according to the above described process. Two or three 0.1 or 0.2 ml increments of 50 mg/l or 25 mg/l phosphonate were added to sample vials and analyzed for phosphonate as described above. The absorbance was measured at 725 nm using a couvette length of 4 cm. The brines used were Delee (a), Thompson (b), Mishriff (e), McElroy (f) and Prudhoe Bay (g). The absorbance vs. concentration of phosphonate added was plotted, as shown in FIGS. 1A and 1B, and the concentration of phosphate or phosphonate extrapolated by setting the Y axis to 0. The plots for deionized water subjected to the same process treatment is shown as lines (d) and (h). Linear regression lines with similar slope with a correlation coefficient better than 0.99 can be used to fit the data and indicates there is no interference due to the different brines.

Analyses were also made by adding orthophosphate instead of diethylenetriaminepenta(methylene phosphonate). When adding orthophosphate instead of phosphonate, the conversion factor to convert phosphate concentration to phosphonate concentration is: mg/l phosphonate = (mg/l $PO_4^{3-}$)(Mol. Wt. Phosphonate/No. phosphorous atoms per phosphonate)/(Mol. Wt. $PO_4^{3-}$) or 1.1979. The data indicates that the digestion of the present process quantitatively converts phosphonate into phosphate.

When the brine contained less than 0.5 mg/l phosphonate, a 100 ml instead of 20 ml sample was used. The reagents in the digestion step were increased fivefold, but the volume of solvent, alcoholic hydrochloric acid and stannous chloride remained the same, resulting in phosphonate concentration in the sample increased by five times.

EXAMPLE II

Figure 2:
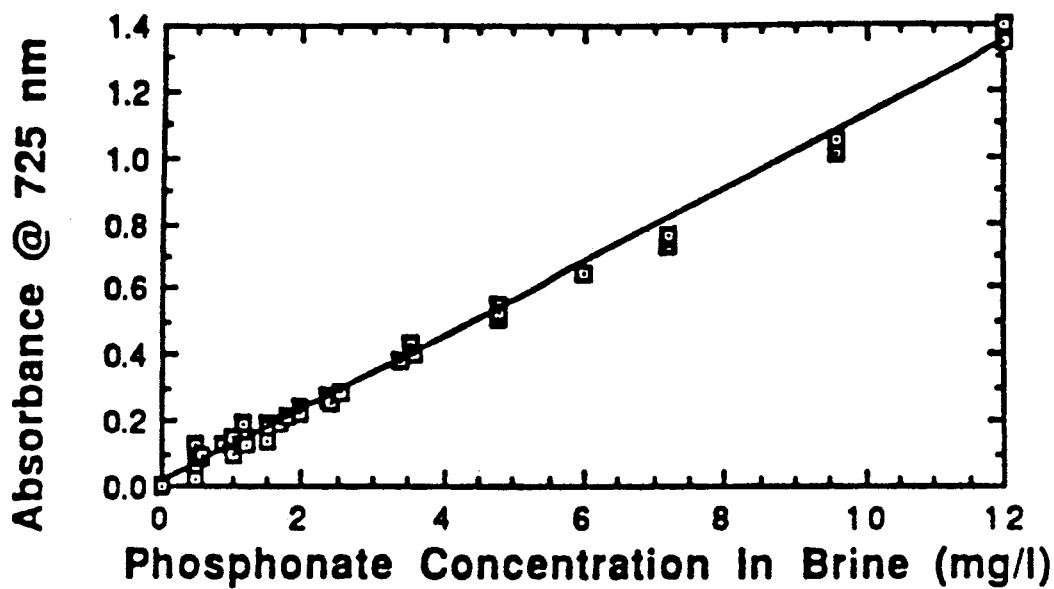
FIG. 2 is a plot of normalized phosphonate concentration as described in Example II.

Additional standard phosphate solutions have been used in the same manner as described in Example I to test the upper detection limits of the process of this invention. The results of the higher standard phosphate solutions and the results from Example I were normalized by subtraction of background absorbance from the data of the brine samples to result in the single plot shown in FIG. 2. A single linear regression line with a correlation coefficient of 0.998 and slope of 0.111 was calculated. The Beer-Lambert Law was obeyed up to about 12 mg/l phosphonate concentration. The lower detection limit is about 0.5 mg/l phosphonate in brine using a 4 cm long light path.

EXAMPLE III

Figure 3:
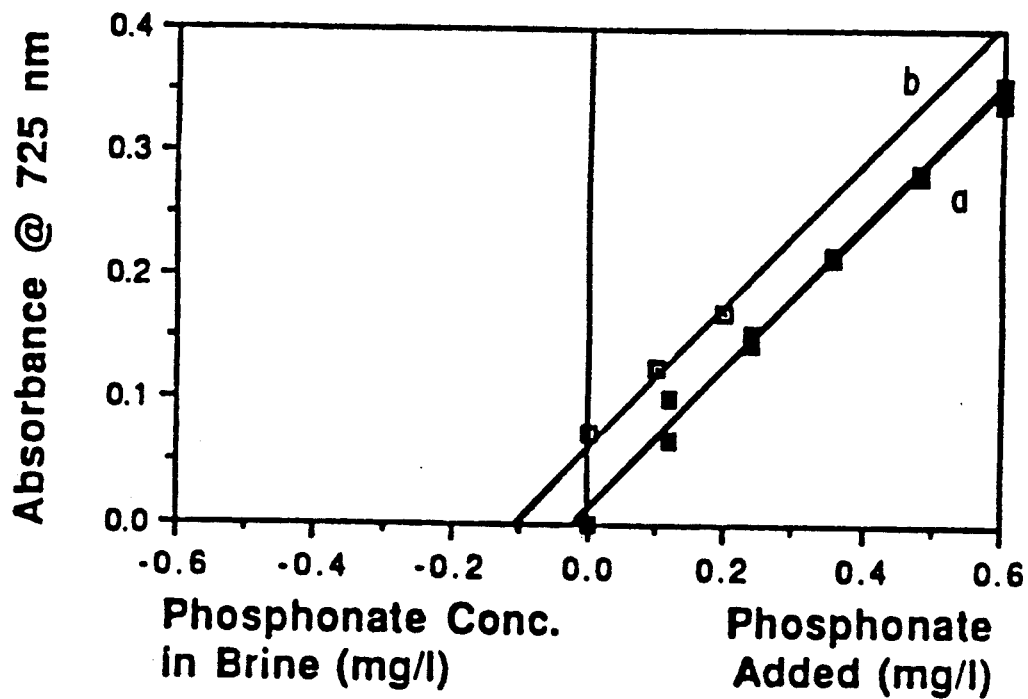
FIG. 3 shows plots of phosphonate concentration using larger sample aliquots as described in Example III.

The sensitivity of the process can be enhanced by using larger sample size and extracting the phosphomolybdate complex into the same organic extractant volume. In the same manner as described in Example I, a 100 ml sample aliquot of Delee brine with a known low phosphonate concentration has been tested to result in a five-fold increase in sensitivity. The results of the Delee brine are shown in FIG. 3 as line (b), with line (a) being deionized water. The slope of the standard addition line is 0.565, 5.1 times the slope of the line in FIG. 2, within the error of the analysis.

EXAMPLE IV

The process of this invention, as described in detail in Example I, was used to monitor the phosphonate concentration in the DOE Geopressured-Geothermal Gladys McCall Design Well in the Crab Lake Field, Cameron Parish, Louisiana, U.S.A. for about six months following an inhibitor squeeze. The phosphonate concentration dropped to about 0.15 mg/l within one month and remained at about that level for an additional five months until the well was shut-in for maintenance and re-squeezed. The 0.15 mh/l phosphonate level is two time the lowest level of inhibitor possible for satisfactory operation as indicated by Mason B. Tomson, Effect of Precipitation Inhibitors on Calcium Carbonate Scal Formation, Journal of Crystal Growth, 62, pgs.

106–112, (1983). As a result of this inhibitor squeeze, brine production was increased from 15,000 to 30,000 BWPD without scale formation. The phosphonate concentration in the brine is summarized in Table 2.

TABLE 2

| VOLUME OF PRODUCED BRINE (bbl) | MEASURED PHOSPHONATE (mg/l) |
|---|---|
| 306 | None |
| 406 | None |
| 806 | 200 |
| 1,026 | 175 |
| 1,086 | 110 |
| 1,146 | 124 |
| 1,206 | 128 |
| 1,266 | 168 |
| 1,326 | 146 |
| 1,366 | 138 |
| 1,406 | 132 |
| 1,506 | 172 |
| 4,750 | 6.4 |
| 48,473 | 0.8 |
| 225,632 | 0.17 |
| 628,401 | 0.13 |
| 4,426,428 | 0.14 |

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of the invention.

We claim:

1. A process for measurement of low levels of phosphate concentrations of down to about 0.1 mg/l in brine, said process comprising the steps:

acidifying promptly upon sampling said brine comprising phosphonates with hydrochloric acid in an amount equivalent to about 0.5 to about 5 ml concentrated hydrochloric acid per 100 ml brine to prevent phosphonate precipitation or absorption;

digesting said hydrochloric acid acidified brine comprising phosphonates in the presence of an oxidizing agent at elevated temperature and pressure for sufficient time to convert substantially all of said phosphonates to orthophosphate;

adding sufficient molybdate salt suitable for reaction with said orthophosphate to form a phosphomolybdate complex;

separating said phosphomolybdate complex using an organic extractant;

adding a color forming reagent to the extracted phosphomolybdate complex for reaction with said phosphomolybdate complex forming a colored solution suitable for absorption spectrophotometry; and measuring the spectrophotometric absorption of said colored solution at or near characteristic absorption peaks, thereby obtaining the amount of phosphonate in said sample by comparison with a known calibration curve.

2. The process of claim 1 wherein said brine is acidified with about 1.0 ml to about 3.0 ml concentrated hydrochloric acid per 100 ml brine.

3. The process of claim 1 wherein said oxidizing agent is selected from the group consisting of potassium persulfate, ammonium persulfate, perchloric acid and nitric acid.

4. The process of claim 3 wherein said oxidizing agent is selected from the group consisting of potassium persulfate and ammonium persulfate.

5. The process of claim 1 wherein said oxidizing agent comprises potassium persulfate in an amount of about 5 mg/ml to about 30 mg/ml.

6. The process of claim 1 wherein said digesting is carried out at a temperature of about 212° to about 300° F.

7. The process of claim 6 wherein said digestion pressure is about 14 to about 30 psi and said digestion is carried out for about 20 to about 60 minutes.

8. A process for measurement of low levels of phosphonate concentrations of down to about 0.1 mg/l in brine, said process comprising the steps:

acidifying promptly upon sampling said brine comprising phosphonates with hydrochloric acid in a sufficient quantity to prevent phosphonate precipitation or adsorption;

digesting said hydrochloric acid acidified brine comprising phosphonates in the presence of an oxidizing agent at elevated temperature and pressure for sufficient time to convert substantially all of said phosphonates to orthophosphate;

adding sufficient molybdate salt suitable for reaction with said orthophosphate to form a phosphomolybdate complex;

separating said phosphomolybdate complex using an organic extractant selected from the group consisting of methyl iso-butyl ketone/cyclohexane mixture, isobutanol/benzene mixture, and ethyl acetate;

adding a color forming reagent to the extracted phosphomolybdate complex for reaction with said phosphomolybdate complex forming a colored solution suitable for absorption spectrophotometry; and measuring the spectrophotometric absorption of said colored solution at or near characteristic absorption peaks, thereby obtaining the amount of phosphonate in said sample by comparison with a known calibration curve.

9. The process of claim 8 wherein said organic extractant is methyl iso-butyl ketone/cyclohexane mixture, each component comprising about 40 to about 60 volume percent of said mixture.

10. The process of claim 1 wherein alcoholic acid is used to maintain the acidity of said extracted phosphomolybdate complex by addition of alcoholic hydrochloric acid having about 30 ml to about 90 ml concentrated hydrochloric acid per about 800 to about 100 ml alcohol, said alcoholic acid added in an amount to achieve acidity of about 0.3 to about 0.5 meq per liter.

11. In the process for measurement of phosphonate concentration in oil or gas well aqueous brine liquid by oxidation of an aliquot sample of said phosphonate to orthophosphate, solvent extraction of orthophosphate complex compound from said aqueous liquids in an organic extractant, and color development of said extracted orthophosphate complex compound for spectrophotometric absorption, the improvement comprising; acidifying said phosphonate sample with hydrochloric acid promptly upon removal from said well, said hydrochloric acid being added in an amount equivalent to about 0.5 to about 5 ml concentrated hydrochloric acid per 100 ml brine and sufficient to prevent phosphonate precipitation or absorption.

12. In the process according to claim 11 wherein said brine is acidified with about 1.0 ml to about 3.0 ml concentrated hydrochloric acid per 100 ml brine.

13. In the process according to claim 11 wherein the hydrochloric acid acidified phosphonate is digested in the presence of an oxidizing agent at elevated temperature and pressure for sufficient time to oxidize substantially all of said phosphonate to orthophosphate.

14. In the process according to claim 13 wherein said oxidizing agent is selected from the group consisting of potassium persulfate, ammonium persulfate, perchloric acid and nitric acid.

15. In the process according to claim 13 wherein said oxidizing agent is selected from the group consisting of potassium persulfate and ammonium persulfate.

16. In the process according to claim 13 wherein said oxidizing agent comprises potassium persulfate in an amount of about 5 mg/ml to about 30 mg/ml.

17. In the process according to claim 13 wherein said digesting is carried out at a temperature of about 212° to about 300° F.

18. In the process according to claim 17 wherein said digestion pressure is about 14 to about 30 psi and said digestion is carried out for about 20 to about 60 minutes.

19. In the process according to claim 11 wherein alcoholic acid is used to maintain the acidity of the orthophosphate complex solution by addition of alcoholic hydrochloric acid having about 30 ml to about 90 ml concentrated hydrochloric acid per about 800 to about 1000 ml alcohol, said alcoholic acid added in an amount to achieve orthophosphate complex solution acidity of about 0.3 to about 0.5 meq per liter.

20. In the process for measurement of phosphonate concentration in oil or gas well aqueous brine liquid by oxidation of an aliquot sample of said phosphonate to orthophosphate, solvent extraction of orthophosphate complex compound from said aqueous liquids in an organic extractant, and color development of said extracted orthophosphate complex compound for spectrophotometric absorption, the improvement comprising; acidifying said phosphonate sample with hydrochloric acid promptly upon removal from said well, said hydrochloric acid being present in a concentration and a quantity and sufficient to prevent phosphonate precipitation or adsorption and said organic extractant being selected from the group consisting of methyl iso-butyl ketone/cyclohexane mixture, and ethyl acetate.

* * * * *